US 6,719,728 B2

(12) United States Patent
Mason et al.

(10) Patent No.: US 6,719,728 B2
(45) Date of Patent: *Apr. 13, 2004

(54) PATIENT-CONTROLLED MEDICATION DELIVERY SYSTEM WITH OVERMEDICATION PREVENTION

(75) Inventors: Bradley R. Mason, Carlsbad, CA (US); Jeffrey T. Mason, Escondido, CA (US)

(73) Assignee: Breg, Inc., Vista, CA (US)

( * ) Notice: Subject to any disclaimer, the term of this patent is extended or adjusted under 35 U.S.C. 154(b) by 311 days.

This patent is subject to a terminal disclaimer.

(21) Appl. No.: 09/924,411

(22) Filed: Aug. 7, 2001

(65) Prior Publication Data
US 2002/0019608 A1 Feb. 14, 2002

Related U.S. Application Data

(63) Continuation-in-part of application No. 09/334,856, filed on Jun. 16, 1999, now Pat. No. 6,270,481.

(51) Int. Cl.[7] .................................................. A61M 5/00
(52) U.S. Cl. ....................................... 604/181; 604/131
(58) Field of Search ............................... 604/131–135, 604/93.01, 181, 122, 124, 125, 187, 257, 264, 30, 32–34, 118, 186, 246–250

(56) References Cited

U.S. PATENT DOCUMENTS

| 1,115,908 | A | 11/1914 | Dees | |
|---|---|---|---|---|
| 1,373,803 | A | 4/1921 | Dunn | |
| 1,930,929 | A | 10/1933 | Eisenberg | 128/218 |
| 2,825,334 | A | 3/1958 | Kas, Sr. | 128/218 |
| 4,253,501 | A | 3/1981 | Ogle | 141/27 |
| 4,425,114 | A | 1/1984 | Schoendorfer et al. | 604/7 |
| 4,456,152 | A | 6/1984 | Young et al. | 222/309 |
| 5,011,477 | A | 4/1991 | Winchell et al. | 604/132 |
| 5,061,243 | A | 10/1991 | Winchell et al. | 604/132 |
| 5,071,409 | A | 12/1991 | Rosenberg | 604/119 |
| 5,484,088 | A | 1/1996 | Martin | 222/402.2 |
| 5,607,418 | A | * 3/1997 | Arzbaecher | 604/891.1 |
| 5,718,354 | A | 2/1998 | Binley | 222/1 |
| 5,779,666 | A | 7/1998 | Teirstein | 604/52 |
| 5,842,611 | A | 12/1998 | Vivier | 222/256 |
| RE36,178 | E | 4/1999 | Freudinger et al. | 222/309 |
| 6,270,481 | B1 | * 8/2001 | Mason et al. | 604/181 |
| 6,283,944 | B1 | * 9/2001 | McMullen et al. | 604/151 |

* cited by examiner

Primary Examiner—Michael J. Hayes
Assistant Examiner—Jennifer Maynard
(74) Attorney, Agent, or Firm—Rodney F. Brown

(57) ABSTRACT

A portable, patient-controlled medication delivery system includes an infusion pump and a catheter assembly. The infusion pump retains a treatment fluid and provides a drive mechanism for delivering the treatment fluid to a patient via the catheter assembly. The infusion pump includes a fluid reservoir, a dosage chamber, a displacement piston displacable within the dosage chamber, a charge flowpath providing fluid communication between the fluid reservoir and the dosage chamber, and a passive flow restrictor positioned in the charge flowpath. An elastic member is also positioned in the infusion pump to exert an elastic displacement force on the displacement piston, which expands the dosage chamber and draws the treatment fluid from the fluid reservoir into the dosage chamber at a charge flow rate controlled by the passive flow restrictor. When an opposing manual displacement force is exerted on the displacement piston, the dosage chamber contracts and discharges the treatment fluid from the dosage chamber to the treatment site.

24 Claims, 5 Drawing Sheets

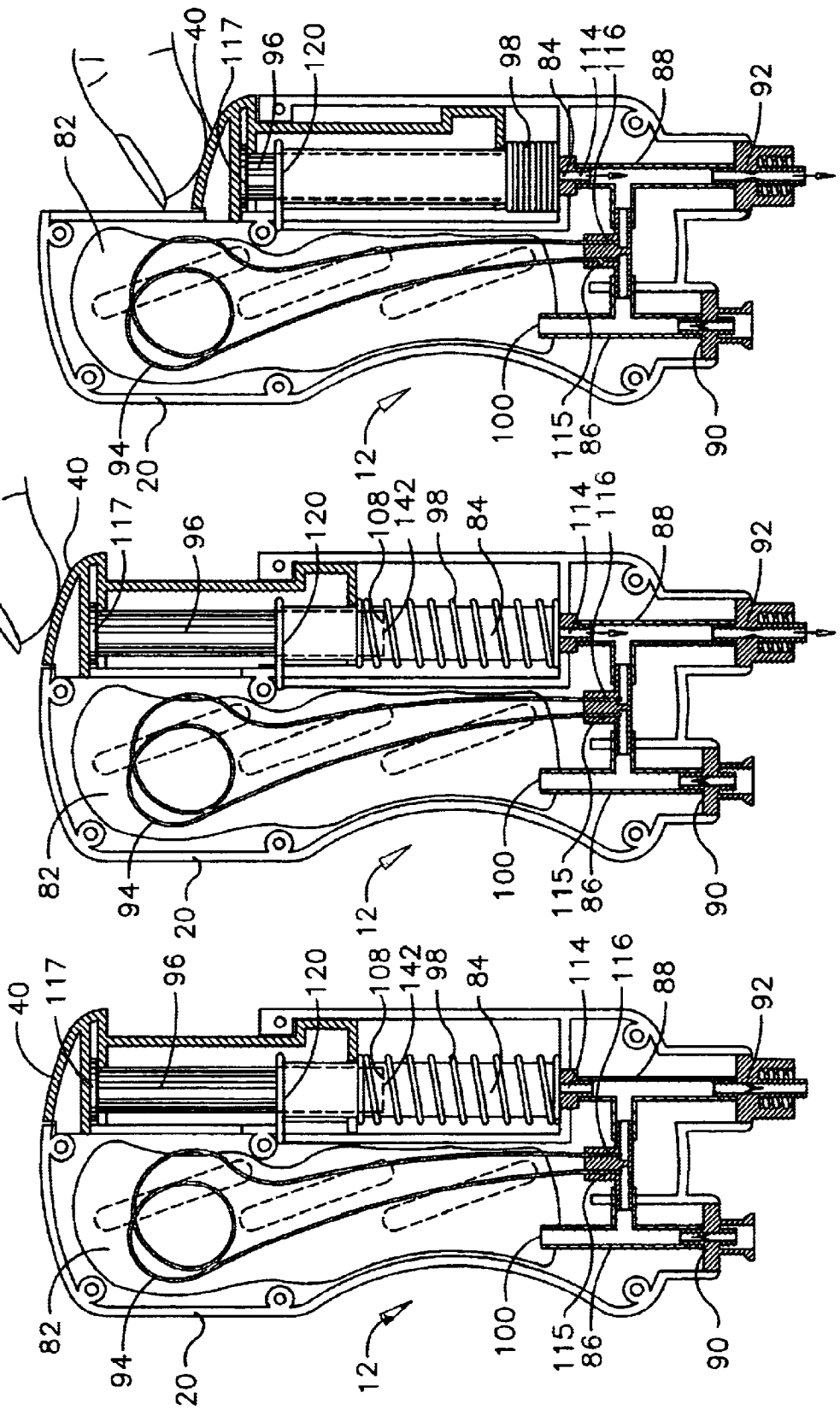

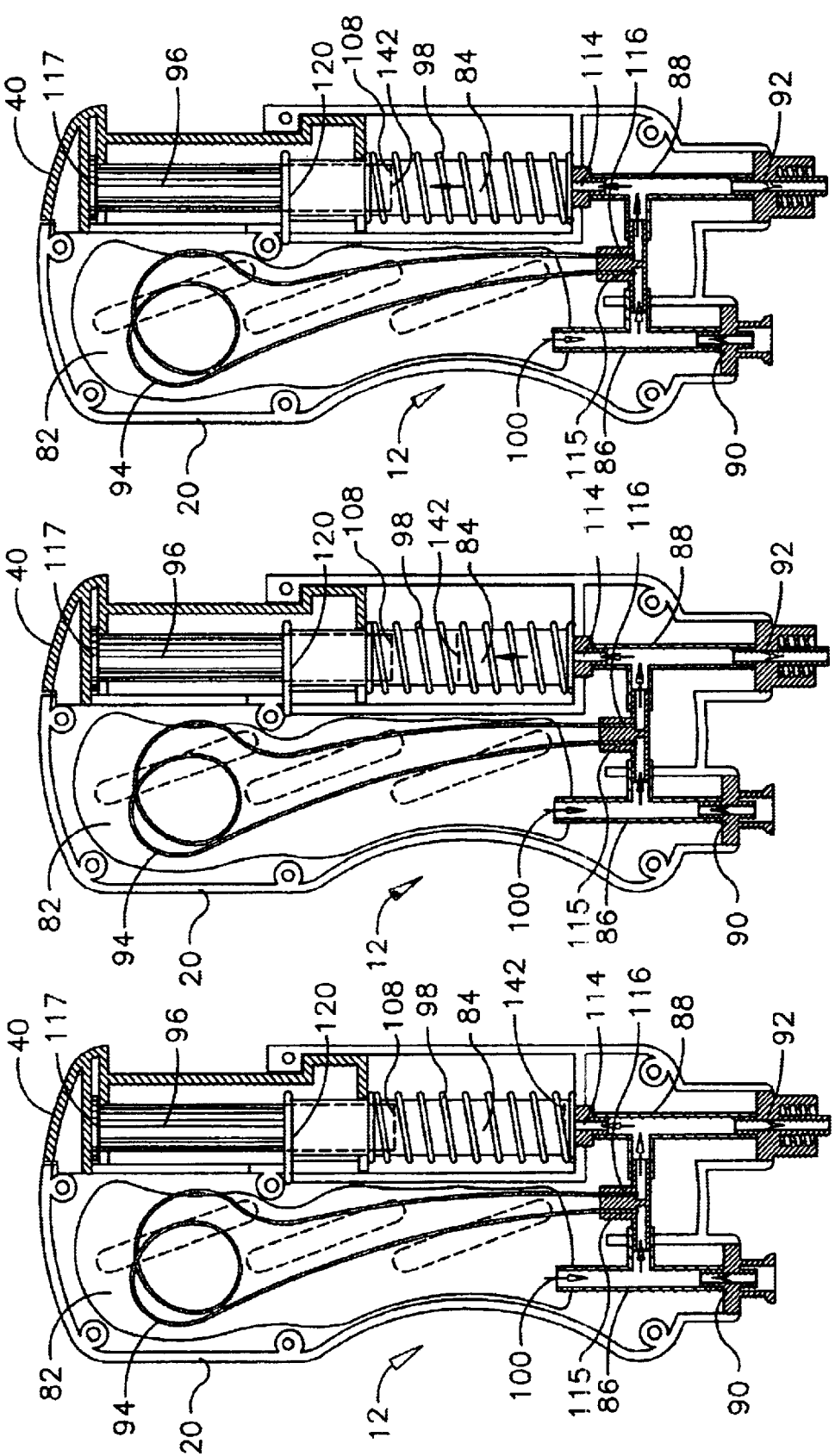

PATIENT-CONTROLLED MEDICATION DELIVERY SYSTEM WITH OVERMEDICATION PREVENTION

This a continuation-in-part application of Ser. No. 09/334,856 filed on Jun. 16, 1999 now U.S. Pat. No. 6,270,481.

TECHNICAL FIELD

The present invention relates generally to a system for delivering medicine to a patient, and more particularly, to a system having a patient-controlled infusion pump which delivers medicine to an internal treatment site.

BACKGROUND OF THE INVENTION

Pain management is an important aspect of post-operative recovery from surgery. Pain management usually begins immediately following the surgical procedure with the administration of narcotics or other pain control medications to the patient while the patient is under the direct supervision of the health care provider. The pain control medications are most commonly administered either orally or by injection.

The proliferation of less-invasive arthroscopic techniques for the surgical repair of many joint or soft tissue injuries and ailments has significantly reduced post-operative recovery times and the attendant pain experienced by the patient. The current trend toward arthroscopic techniques frequently enables surgical procedures to be performed on an outpatient basis or with shortened post-operative hospital stays. As a result, the bulk of the post-operative recovery time is spent in the home or even in the workplace. One goal of home recovery is to phase the patient back into routine physical activities relatively quickly as a means of shortening the post-operative recovery time.

Since the patient is generally not under the direct supervision of the health care provider when in the home or workplace, the responsibility for administering pain control medications falls on the patient in these environments. Nearly all self-administered pain control medications are oral medications because most individuals lack the requisite knowledge, skill, and experience to self-administer pain control medications by injection. Unfortunately, however, pain control medications administered orally are transported throughout the body and correspondingly affect the entire body, often causing undesirable side effects such as drowsiness, disorientation, nausea, constipation or vomiting. In contrast, injected pain control medications can be administered more locally than orally administered medications, thereby frequently avoiding the undesirable side effects of oral medications. In addition, injected pain control medications reach the treatment site more rapidly and in greater concentrations than oral medications, rendering injected pain control medications a more effective pain control therapy. Although advantageous, injected pain control medications are nevertheless not feasible for most individuals not under the direct supervision of health care providers for the reasons set forth above. In addition, it has been found in many instances that pain control medication is most effective if periodically injected into the treatment site as a single relatively large pulse, termed a bolus dosage, when the patient senses the oncome of discomfort due to pain rather than being continuously injected into the treatment site over time. However, if the patient is allowed to self-administer injection of the pain control medication on an as needed basis in the absence of supervision of a health care provider, the risk of overmedication is significant.

The present invention recognizes a need for a device which enables the patient to effectively self-administer medication by injection even when the patient lacks the requisite knowledge, skill or experience to perform injections. Accordingly, it is an object of the present invention to provide a medication delivery system, wherein operation of the system is controlled by the patient. More particularly, it is an object of the present invention to provide such a medication delivery system, wherein the patient controls the injection of the medication directly into a treatment site of the patient. It is another object of the present invention to provide such a medication delivery system, wherein the system can be effectively operated by a patient lacking any specific medical knowledge, skill or experience in performing injections. It is another object of the present invention to provide such a medication delivery system, wherein the system automatically prevents the patient from overmedicating oneself. It is still another object of the present invention to provide such a medication delivery system, wherein the system is fully self-contained and portable so that the system can be worn by the patient during routine physical activity. It is yet another object of the present invention to provide such a medication delivery system, wherein the system may be cost-effectively disposed after a single patient use.

These objects and others are accomplished in accordance with the invention described hereafter.

SUMMARY OF THE INVENTION

The present invention is a portable, patient-controlled medication delivery system, which enables a patient to self-administer a liquid medical treatment fluid to a treatment site. The medication delivery system includes an infusion pump and a medicine catheter. The medicine catheter has a first end, which is positionable in the treatment site of the patient, and a second end, which is in fluid communication with the infusion pump to provide fluid communication between the infusion pump and the treatment site. The infusion pump retains a total charge of the treatment fluid comprising a plurality of full or partial dosages and provides a drive mechanism for delivering one or more dosages of the treatment fluid to the treatment site.

The infusion pump has a flexible fluid reservoir, a rigid dosage chamber, a displacement piston slidably displacable within the dosage chamber, and a charge flowpath, which provides fluid communication between the fluid reservoir and the dosage chamber. The charge flowpath includes a passive flow restrictor having a fixed length and a fixed cross-section. An elastic member is also positioned in the infusion pump and connected to the displacement piston. The elastic member is transitionable from a more stressed position to a less stressed position to charge the dosage chamber with the treatment fluid from the fluid reservoir at a charge flow rate controlled by the passive flow restrictor. The fixed length and fixed cross-section of the passive flow restrictor are selected to produce the controlled charge flow rate of the treatment fluid. The elastic member is further transitionable from the less stressed position to the more stressed position to discharge the treatment fluid from the dosage chamber via the fluid outlet. The elastic member displaces the displacement piston in a first direction away from the fluid outlet to expand the dosage chamber when the elastic member transitions from the more stressed position to the less stressed position. Conversely, the displacement piston is manually displaced in a second direction toward the fluid outlet to contract the dosage chamber when the elastic member transitions from the less stressed position to the more stressed position.

The fluid reservoir is preferably a substantially inelastic bladder having a fluid capacity substantially greater than the fluid capacity of the dosage chamber. In particular, the fluid reservoir preferably has a capacity for a plurality of full dosages of the treatment fluid, whereas the dosage chamber has a capacity for only one full dosage of the treatment fluid. The elastic member is preferably a coiled spring connected to the displacement piston by engagement with a manually displacable actuator button which in turn engages the displacement piston. The flow restrictor is preferably a continuously open length of flexible tubing.

In operation, one end of the medicine catheter is placed in the treatment site and the other end is placed in fluid communication with the infusion pump. The fluid reservoir is filled with the total charge of the treatment fluid and the dosage chamber is charged with a treatment fluid dosage of the treatment fluid form the fluid reservoir. The infusion pump is mounted on the body of the patient and the patient self-administers the treatment fluid by manually depressing the actuator button. The actuator button drives the displacement piston through the dosage chamber in the second direction, while transitioning the elastic member from the less stressed position to the more stressed position. The displacement piston contracts the dosage chamber and displaces the treatment fluid dosage from the dosage chamber into the treatment site via the medicine catheter.

The dosage chamber automatically recharges with the treatment fluid when the actuator button is released. Release of the actuator button enables the elastic member to automatically transition from the more stressed position to the less stressed position, thereby displacing the displacement piston in the first direction within the displacement chamber. Displacement of the displacement piston creates a void in the dosage chamber of extremely reduced pressure relative to the fluid reservoir. The extremely reduced pressure preferably constitutes a near total vacuum. In the meantime, the fluid reservoir is maintained at substantially ambient atmospheric pressure. The positive pressure differential created between the fluid reservoir and the dosage chamber drives the treatment fluid from the fluid reservoir through the charge flowpath into the dosage chamber at the charge flow rate controlled by the passive flow restrictor. The controlled charge flow rate is preferably substantially constant and corresponds to a desired dosage rate of the treatment fluid to the patient.

The present invention will be further understood from the drawings and the following detailed description.

BRIEF DESCRIPTION OF THE DRAWINGS

FIGS. 5A–F are diagrammatic rear views of the infusion pump of FIG. 1 shown in a sequence of operating modes which comprise a single operating cycle.

DESCRIPTION OF PREFERRED EMBODIMENTS

Figure 1:
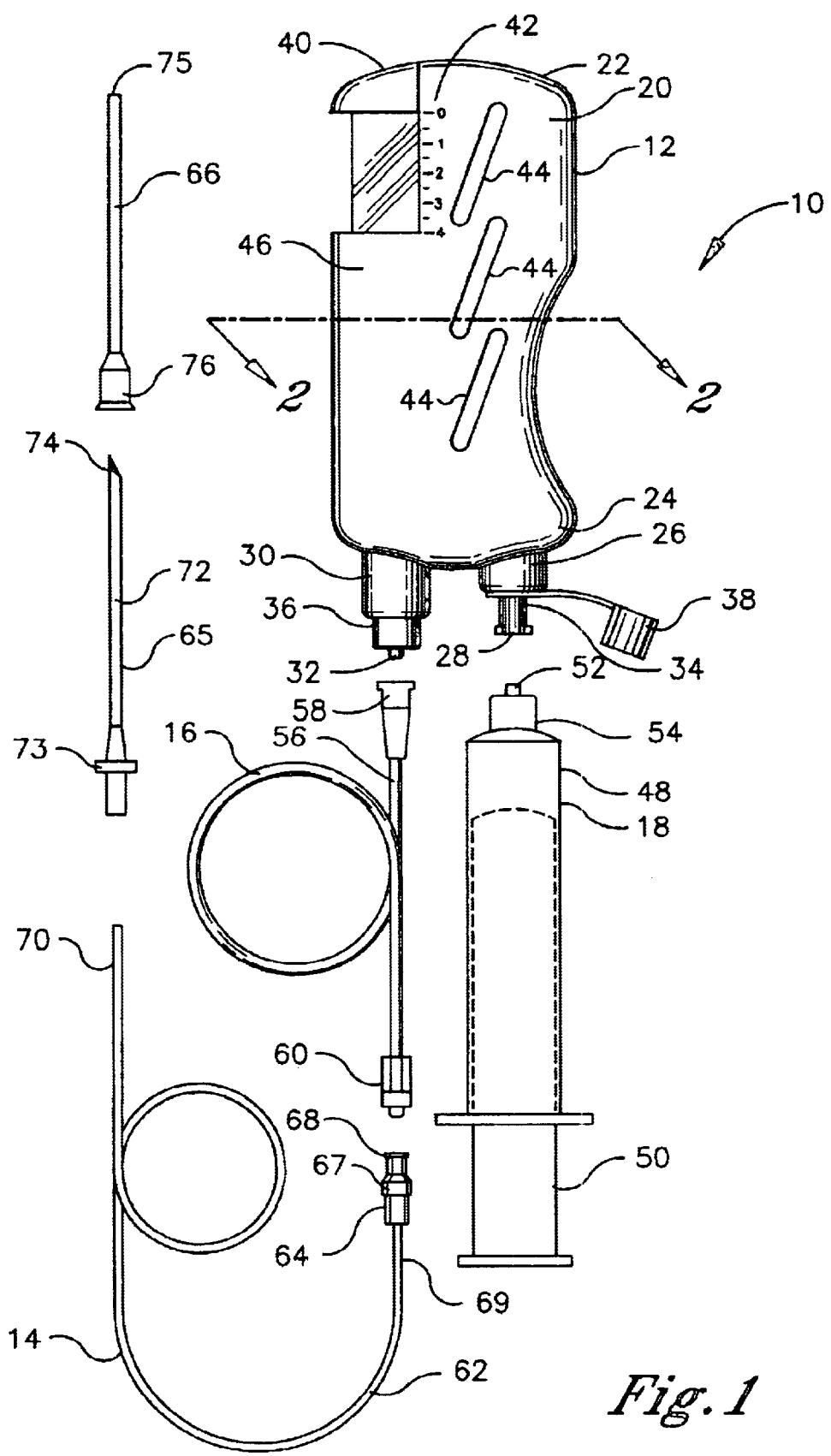
FIG. 1 is an exploded front view of a medication delivery system of the present invention.

Referring initially to FIG. 1, a medication delivery system of the present invention is shown and generally designated 10. The system 10 comprises an infusion pump 12, a catheter assembly 14, an extension tubing set 16 and a filling syringe 18. The infusion pump 12 is shown in FIG. 1 in an operative orientation, wherein the infusion pump 12 is oriented for discharging a desired liquid medicine to a treatment site. The top and bottom of the infusion pump 12 are denoted hereafter with reference to the operative orientation. The front and back of the infusion pump 12 are denoted hereafter with reference to the body of a patient on which the system 10 is mounted. The front of the infusion pump 12 faces away from the body of the patient and the rear of the infusion pump 12 faces toward the body of the patient.

The infusion pump 12 is a portable self-contained unit enclosed within a rigid durable plastic housing 20 having a top portion 22 and a bottom portion 24. The bottom portion 24 is provided with a first appendage 26 which retains a medicine inlet port 28 and a second appendage 30 which retains a medicine outlet port 32. The first appendage 26 also retains a first pump coupling element 34 for coupling the infusion pump 12 with the filling syringe 18, while the second appendage 30 retains a second pump coupling element 36 for coupling the infusion pump 12 with the extension tubing set 16. The medicine inlet port 28 has a selectively removable protective cap 38 which is tethered to the first pump coupling element 34, retaining the protective cap 38 in engagement with the infusion pump 12 when the protective cap 38 is removed from the medicine inlet port 28. A slidably displacable actuator button 40 is positioned in the top portion 22 of the housing 20. The actuator button 40 is shown in a fully extended upward position. A graduated scale 42 is provided along a length of the housing 20 adjacent to the actuator button 40, indicating the degree to which the actuator button 40 is slidably displaced downward toward the bottom portion 24 of the housing 20, as will be described hereafter. Viewing windows 44 are also provided in the front face 46 of the housing 20 to enable the user to observe the volume of medicine residing in the infusion pump 12.

The filling syringe 18 is a conventional disposable plastic syringe with a cylinder 48 having a relatively large capacity, for example 60 cc. The filling syringe 18 also has a plunger 50, a fluid orifice 52, and a syringe coupling element 54 associated with the fluid orifice 52, which enable the practitioner to draw the desired medicine into the cylinder 48 from a source (not shown) and to displace the medicine from the cylinder 48 into the medicine inlet port 28 of the infusion pump 12. The fluid orifice 52 is sized and configured to be compatible with the medicine inlet port 28 and the syringe coupling element 54 is sized and configured to be compatible with the first pump coupling element 34, thereby facilitating transfer of the medicine from the filling syringe 18 into the infusion pump 12. The first pump coupling element 34 is preferably a female Luer lock fitting having external locking tabs. The medicine inlet port 28 is concentrically disposed within the first pump coupling element 34. The syringe coupling element 54 is preferably a male Luer lock fitting having an internal thread which receives the external locking tabs of the female first pump coupling element 34 to fix the alignment of the fluid orifice 52 and the medicine inlet port 28 when filling the infusion pump 12 with the medicine from the filling syringe 18.

The extension tubing set 16 includes a length of an extension tube 56, a first extension coupling element 58 secured to one end of the extension tube 56, and a second extension coupling element 60 secured to the opposite end of the extension tube 56. The extension tube 56 is preferably a substantially uniform, transparent or translucent, flexible, plastic tubing. The extension tube 56 is sized to be compatible with the medicine outlet port 32 and the first extension coupling element 58 is sized and configured to be compatible with the second pump coupling element 36, thereby facilitating transfer of the medicine from the infusion pump 12 to the extension tube 56 and thereafter to the interconnected catheter assembly 14. For example, the extension tube 56 may be a relatively large vinyl tubing of the type termed in the art as "microbore tubing" which is has an outside diameter of about 0.094 inches. Thus, the extension tube 56 has a relatively large flow cross-section which enables the rapid displacement of relatively large volumes of the liquid medicine from the infusion pump 12 through the extension tube 56 as will be described hereafter. The second pump coupling element 36 is preferably a male Luer lock fitting having an internal thread and the medicine outlet port 32 is concentrically disposed within the second pump coupling element 36 and extends therefrom. The first extension coupling element 58 is preferably a female Luer lock fitting having external locking tabs which are received by the internal thread of the male second pump coupling element 36 to fix the alignment of the extension tube 56 and the medicine outlet port 32 when the infusion pump 12 is operative.

The catheter assembly 14 includes a medicine catheter 62, a catheter connector 64, an introducer needle 65, and an insertion catheter 66. The medicine catheter 62 is formed from a length of substantially uniform, transparent or translucent, thin-walled, highly flexible, plastic tubing. The medicine catheter 62 is typically dimensionally smaller than the extension tube 56 to minimize disruption and promote healing of the treatment site in which the medicine catheter 62 resides. For example, the medicine catheter 62 may be a 16 to 20 gauge polyurethane tubing. A preferred medicine catheter 62 is a 16 gauge tubing having a relatively small outside diameter of about 0.057 inches, a relatively small inside diameter of about 0.036 inches and a durameter flexibility of about 65A. The medicine catheter 62 has sufficient flexibility to follow a tortuous path, if desired, while resisting kinking and blockage of flow during operation of the medication delivery system 10 despite the relatively small flow cross-section of the medicine catheter 62.

The catheter connector 64 provides a compression fitting 67 and a catheter coupling element 68. The compression fitting 67 fixably attaches the catheter connector 64 to the first bare open end 69 of the medicine catheter 62 and the catheter coupling element 68 engages the second extension coupling element 60 of the extension tubing set 16. The catheter coupling element 68 is preferably a female Luer lock fitting having external locking tabs. The second extension coupling element 60 is preferably a male Luer lock fitting having an internal thread which receives the external locking tabs of the catheter coupling element 68. The catheter connector 64 enables the practitioner to connect the medicine catheter 62 to the extension tube 56, preferably after the opposite second bare open end 70 of the medicine catheter 62 has been placed in the treatment site of a patient by means of the introducer needle 65 and insertion catheter 66.

The introducer needle 65 is a hollow rigid metal needle having an elongated body 72, a widened stop 73 at one end, and a sharpened tip 74 at the other end for puncturing an opening in the skin of a patient and penetrating through the opening and surrounding tissue to the internal treatment site. The insertion catheter 66 is a tubular plastic sleeve having a slight taper 75 at one end and a widened tubular stop 76 at the other end. The insertion catheter 66 has an inside diameter slightly greater than the outside diameter of the introducer needle 65 and a length slightly less than that of the introducer needle 65 so that the introducer needle 65 can be fitted through the insertion catheter 66 until the stops 73, 76 engage one another. The sharpened tip 74 extends from the tapered end 75 of the insertion catheter 66 when the stops 73, 76 are in engagement. The inside diameter of the insertion catheter 66 is also slightly greater than the outside diameter of the medicine catheter 62 so that the end 70 of the medicine catheter 62 can be fitted through the insertion catheter 66 when the introducer needle 65 is withdrawn from the insertion catheter 66. The relative sizing and configuration of the introducer needle 65, insertion catheter 66 and medicine catheter 62 enable placement of the medicine catheter 62 in the treatment site of the patient in a manner described hereafter.

Figure 2:
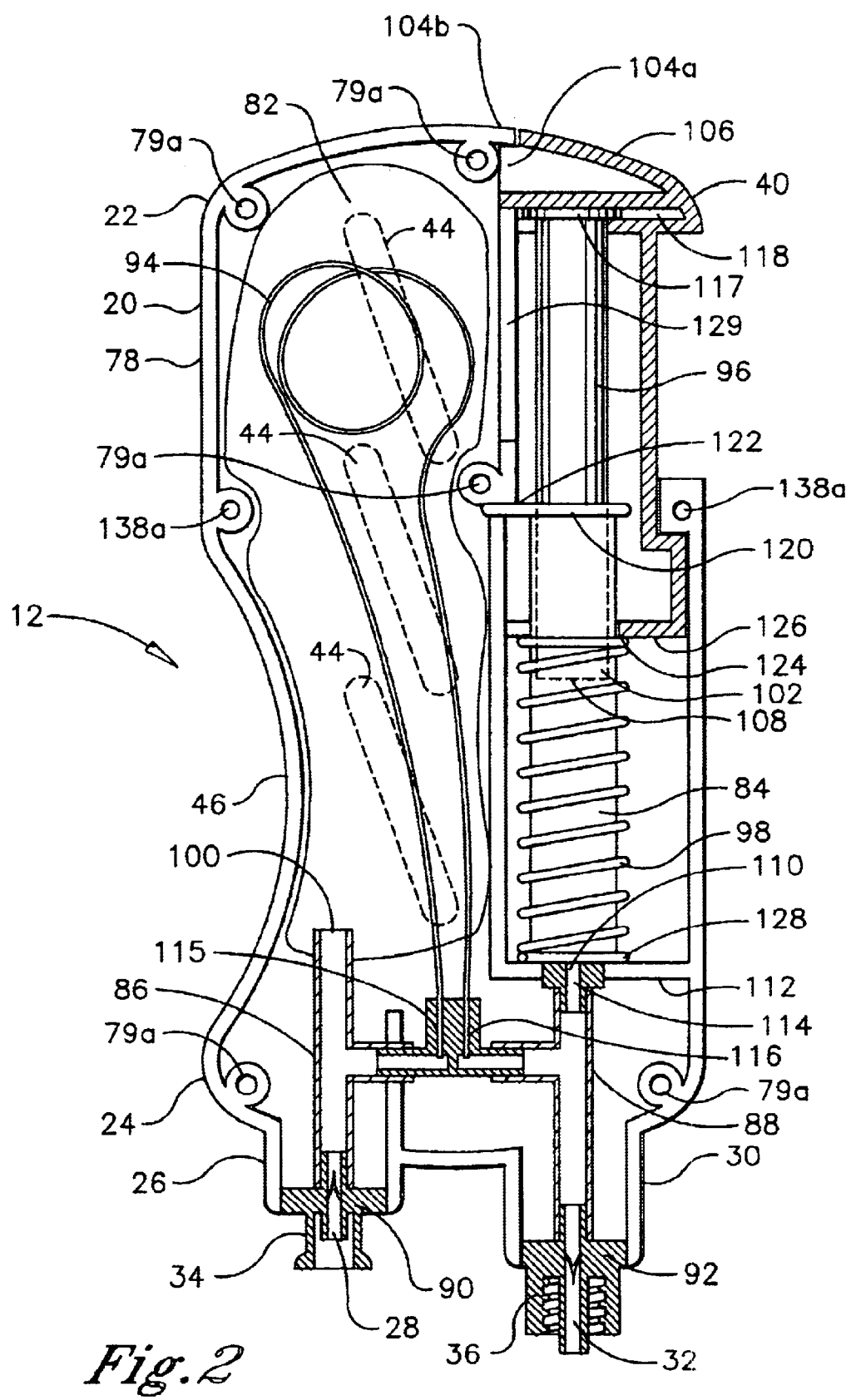
FIG. 2 is a rear view of an infusion pump included in the medication delivery system of FIG. 1 taken in partial cross-section along line 2—2.

Details of the construction of the infusion pump 12 are described below with reference to FIG. 2, wherein the elements of FIG. 2 which are common to FIG. 1 have the same reference characters as FIG. 1. The infusion pump 12 generally includes a fluid flowpath and a fluid drive mechanism contained within the housing 20. The housing 20 is preferably fabricated from two substantially symmetrical half sections. One half section contains the front face 46 and the opposing half section contains the back face 77 (shown in FIG. 4). The half sections 46, 77 are joined together along the peripheral edge 78 during assembly of the infusion pump 12 and fastened by means of screw holes 79*a* in the front face 46, screw holes 79*b* in the back face 77, and screws 80 (shown in FIG. 4). FIG. 2 shows the infusion pump 12 with the back face 77 removed and a number of components in cross-section for clarity. The fluid flowpath comprises a fluid reservoir 82, a dosage chamber 84, first and second tee junctions 86, 88, first and second one-way check valves 90, 92, and a flow restrictor 94. The fluid drive mechanism comprises a displacement piston 96 and a biasing spring 98.

The fluid reservoir 82 is a fluid-tight vessel and preferably a bladder which is transparent or translucent. The bladder is formed from a flexible, yet relatively inelastic plastic material, such as welded vinyl sheeting. Alternatively, the bladder is formed from an elastic material such as an elastomer. However, the elastic material is preferably not stretched or otherwise stressed outwardly during operation of the medication delivery system 10 such that the bladder does not elastically expand at any time during operation of the system 10. The fluid reservoir 82 has a single reservoir port 100 positioned at the bottom end. The fluid reservoir 82 is sized to have a capacity which accommodates a predetermined volume of a total medicine charge to the infusion pump 12. For example, the predetermined volume of the total medicine charge to the infusion pump 12 may be 50 cc. The first tee junction 86 provides fluid communication between the medicine inlet port 28 and the reservoir port 100. The first one-way check valve 90 is positioned across the medicine inlet port 28 and is biased in the closed position. When the first valve 90 is subjected to an inward (upward) force sufficient to overcome the biasing force, the first valve 90 opens permitting fluid flow from the exterior of the housing 20 through the medicine inlet port 28, first tee junction 86, and reservoir port 100 into the fluid reservoir 82. However, the first valve 90 remains closed at all other times even when subjected to outward (downward) forces, thereby preventing fluid flow from the fluid reservoir 82 through the medicine inlet port 28 to the exterior of the housing 20.

The dosage chamber 84 and displacement piston 96 are cooperatively configured in the manner of a syringe cylinder and plunger. Both the dosage chamber 84 and displacement piston 96 are formed from a durable rigid plastic which is preferably transparent or translucent. A slidably displacable elastomeric seal 102 is positioned at the bottom end of the displacement piston 96 to maintain a fluid seal between the wall of the dosage chamber 84 and the displacement piston 96. It is noted that the dosage chamber 84 has a variable volume which varies as a function of the vertical position of the displacement piston 96 relative to the fixed wall of the dosage chamber 84. The dosage chamber 84 has a maximum volume, i.e., capacity, which correlates to a fully extended upward position of the displacement piston 96. The fully extended upward position of the displacement piston 96 is reached when a first stop 104a on the top end 106 of the actuator button 40 engages a corresponding first stop 104b on the housing 20. Conversely, the dosage chamber 84 has a minimum volume, typically approaching zero, which correlates to the fully depressed downward position of the displacement piston 96. The fully depressed downward position is reached when the bottom end 108 of the displacement piston 96 reaches the bottom end 110 of the dosage chamber 84 and a second stop 111a on the top end 106 of the actuator button 40 engages a corresponding second stop 111b on the housing 20. A frame 112 is provided in the interior of the housing 20 which seats the dosage chamber 84, the displacement piston 96, and the actuator button 40 and maintains the alignment thereof.

The dosage chamber 84 and displacement piston 96 are preferably configured such that the maximum volume of the dosage chamber 84 corresponds identically to a predetermined volume of a full dosage of the medicine. The maximum volume of the dosage chamber 84 and correspondingly the predetermined volume of a full dosage of the medicine is typically sized relatively large, yet substantially smaller than the volume of the total medicine charge to the infusion pump 12. In particular, the maximum volume of the dosage chamber 84 and correspondingly the predetermined volume of a full dosage of the medicine is preferably equal to a recommended bolus dosage of the medicine. For example, the maximum volume of the dosage chamber 84 and correspondingly the predetermined volume of a full dosage of the medicine may be sized within a range between about 1 to 10 cc, preferably between about 2 and 6 cc, and most preferably about 4 cc. Thus, in accordance with the present example, a range between about 5 and 50, preferably between about 8 and 25, and most preferably about 12 full dosages of the medicine are included in the total medicine charge.

The dosage chamber 84 has a single dosage port 114 positioned at the bottom end 110 of the dosage chamber 84. The second tee junction 88 provides fluid communication between the medicine outlet port 32 and the dosage port 114. The second one-way check valve 92 is positioned across the medicine outlet port 32 and is biased in the closed position. When the second valve 92 is subjected to an outward (downward) force sufficient to overcome the biasing force, the second valve 92 opens permitting fluid flow from the dosage chamber 84 through the dosage port 114, second tee junction 88, and medicine outlet port 32 into the extension tube 56. However, the second valve 92 remains closed at all other times even when subjected to inward (upward) forces, thereby preventing fluid flow from the extension tube 56 into the infusion pump 12.

The portion of the fluid flowpath between the fluid reservoir 82 and the dosage chamber 84 is termed the charge flowpath and enables fluid flow from the fluid reservoir 82 to the dosage chamber 84 at a maximum charge flow rate determined by the configuration of the charge flow path. The charge flowpath includes in series the reservoir port 100, the first tee junction 86, the flow restrictor 94, the second tee junction 88 and the dosage port 114. The flow restrictor 94 extends from a flow restrictor port 115 in the first tee junction 86 to a flow restrictor port 116 in the second tee junction 88. The flow restrictor 94 is termed a passive device, defined herein as a device which does not require moving parts to perform its designated function described below. The preferred flow restrictor 94 is a flexible transparent tubing having a fixed length and a fixed inside diameter. The flow restrictor 94 is continuously open along its length and is coiled, enabling its relatively long fixed length to fit within the housing 20. The flow restrictor 94 has a relatively small inside diameter, which provides a substantial size restriction in the cross-section of the charge flowpath. Since the maximum charge flow rate is a function of both the length and inside diameter of the flow restrictor 94, it is within the purview of the skilled practitioner applying the teaching herein to select the length and inside diameter of the flow restrictor 94, which achieves a desired maximum charge flow rate.

For example, if a preferred maximum charge flow rate of about 7 to 8 cc per hour is desired, a flow restrictor may be selected having an inside diameter on the order of about 0.005 inches and a length of about 10 to 12 inches. By comparison the inside diameter of the next smaller remaining element of the fluid flowpath is typically not less than about 0.050 inches, a factor of about 10 times larger than the exemplary flow restrictor. Alternatively, the above-recited preferred maximum charge flow rate can be achieved by selecting, within limits, a shorter and narrower flow restrictor or a longer and wider flow restrictor than the exemplary flow restrictor recited above. For example, the relatively long length of coiled flexible tubing shown herein can be replaced by a relatively short length of a straight rigid glass tube, having a substantially smaller inside diameter than the flexible tubing. However, it is generally preferable to avoid over-constricting the inside diameter of the flow restrictor because the flow restrictor may become susceptible to plugging. Although a broad range of maximum charge flow rates are possible in accordance with the teaching of the present invention, as a rule the maximum charge flow rate should preferably not exceed 12 cc per hour to prevent overmedication.

In any case, it is apparent from the present teaching that the skilled practitioner observes the direct relationship between inside diameter and charge flow rate and the inverse relationship between length and charge flow rate in selecting the dimensions of the flow restrictor for a desired maximum charge flow rate. By appropriately selecting the dimensions of the flow restrictor 94, the practitioner is able to establish a desired maximum charge flow rate of the medicine from the fluid reservoir 82 to the dosage chamber 84, e.g., not greater than 12 cc per hour, which substantially prevents the patient from overmedicating oneself. It is understood from the above that the dimensions and charge flow rate of the flow restrictor 94 are not precisely limited. The exemplary values set forth above provide guidance, but it is within the purview of the skilled practitioner to select alternate dimensions of the flow restrictor 94, which bring about a desired maximum charge flow rate.

With continued reference to FIG. 2, the top end 117 of the displacement piston 96 is received by a slot 118 formed in the top end 106 of the actuator button 40 to fixably engage the displacement piston 96 and the actuator button 40, providing synchronous displacement thereof. The top end 120 of the dosage chamber is received by a slot 122 formed in the frame 112 to fixably engage the dosage chamber 84 and the housing 20. The biasing spring 98 is a coiled metal spring. The top end 124 of the biasing spring 98 engages the bottom end 126 of the actuator button 40 and the bottom end 128 of the biasing spring 98 engages the frame 112 so that the biasing spring 98 substantially encircles the exterior of the dosage chamber 84. Thus, the displacement piston 96, the actuator button 40, and the top end 124 of the biasing spring 98 are fixed relative to each other and are synchronously displacable relative to the housing 20 and the bottom end 128 of the biasing spring 98. The biasing spring 98 is substantially relaxed or less stressed when the biasing spring 98 is in the expanded position and the actuator button 40 and displacement piston 96 are in the fully extended upward position. Conversely, the biasing spring 98 is substantially more stressed when the biasing spring 98 is compressed and the actuator button 40 and displacement piston 96 are in a depressed downward position.

The biasing spring 98 exerts an expansion or displacement force on the actuator button 40 and displacement piston 96 whenever the biasing spring 98 is compressed which functions to bias the actuator button 40 and displacement piston 96 toward their fully extended upward position shown in FIG. 2. The frame 112 receives the bottom end 126 of the actuator button 40 and provides sufficient clearance to permit downward displacement of the actuator button 40 into the housing 20 when the user depresses the actuator button 40 and compresses the biasing spring 98. The frame 112 also has a groove 129 formed therein which serves as a guide for the stop 104b as it is slidably displaced in correspondence with the actuator button 40. It is noted that the biasing spring 98 must be provided with sufficient strength to generate an expansion force when compressed, which overcomes the friction forces occurring during active operation of the infusion pump 12 and which overcomes the ambient atmospheric pressure.

Figures 3, 4:
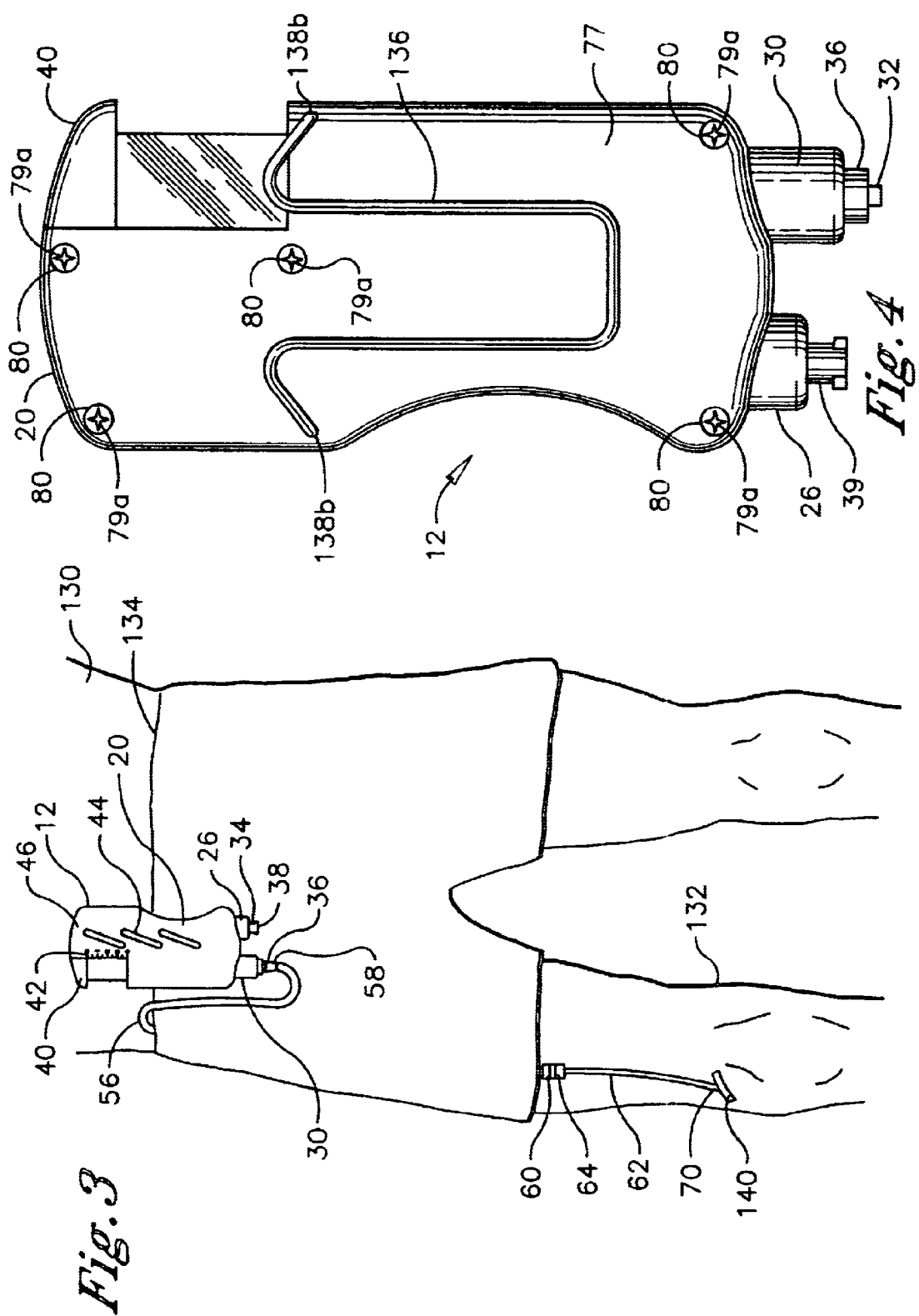
FIG. 3 is a perspective view of the medication delivery system of FIG. 1 operatively positioned on the body of a patient.
FIG. 4 is a rear view of the infusion pump of FIG. 1.

Setup and operation of the medication delivery system 10 is described hereafter with additional reference to FIGS. 3–5, wherein the elements of FIGS. 3–5 which are common to FIGS. 1 and 2 have the same reference characters as FIGS. 1 and 2. In general, setup of the system 10 is performed by filling the infusion pump 12 with a desired liquid medicine, mounting the system 10 on the body of a patient with the medicine catheter 62 in place in a desired internal treatment site, and interconnecting the components of the system 10. Operation of the system 10 is performed by sequentially delivering dosages of the medicine from the infusion pump 12 to the treatment site over time via the medicine catheter 62. In a preferred application of the system 10, the medicine is a local anesthetic for managing post-operative pain and the treatment site is a surgical wound. Setup of the system 10 is preferably performed by a health care provider, while operation of the system 10 may be under the control of the patient.

Referring to FIGS. 1 and 2, setup is initiated by adding a total medicine charge to the cylinder 48 of the filling syringe 18. An exemplary total medicine charge is 50 cc of the local analgesic bupivacaine in a liquid state at a selected concentration such as 0.25% or 0.75%. The protective cap 38 is removed from the medicine inlet port 28 and the syringe coupling element 54 of the filling syringe 18 is engaged with the first pump coupling element 34. The plunger 50 is fully depressed, opening the first valve 90 and driving the total medicine charge from the cylinder 48 through the medicine inlet port 28 and reservoir port 100 into the fluid reservoir 82. The total medicine charge preferably occupies the fluid reservoir 82 without substantially elastically expanding the walls of the fluid reservoir 82. Accordingly, the walls of the fluid reservoir 82 do not apply a substantial inward compression force to the total medicine charge residing therein. The total medicine charge is maintained in the fluid reservoir 82 thereafter under essentially unpressurized conditions, i.e., at ambient atmospheric pressure.

After the total medicine charge is displaced into the fluid reservoir 82, the first valve 90 closes, the syringe coupling element 54 and first pump coupling element 34 are disengaged, and the protective cap 38 is replaced over the medicine inlet port 28. The first extension coupling element 58 of the extension tubing set 16 is then connected to the second pump coupling element 36 and the system 10 is primed for operation by purging all of the air trapped within the system 10. Purging is effected by fully depressing the actuator button 40 while the infusion pump 12 is inverted so that air exits the system 10 via the open second extension coupling element 60 of the extension tubing set 16. Subsequent release of the actuator button 40 causes initial charging of the dosage chamber 84 with the liquid medicine in a manner described below with reference to the dosage charge mode of operation.

Referring to FIGS. 3 and 4, setup continues by mounting the infusion pump 12 on the body 130 of the patient and placing the medicine catheter 62 in the desired treatment site. The medicine catheter 62 is shown placed in the knee joint 132 for purposes of illustration, but it is understood that the medicine catheter 62 can alternatively be placed in other internal locations of the body 130 where treatment is desired. The infusion pump 12 is preferably mounted on the body 130 by releasably attaching the infusion pump 12 to the dressing for the treatment site or an article of clothing worn by the patient, such as a trouser waistband 134 or the like. Releasable attachment is enabled by a mount, which is a clip 136 extending from the back face 77 of the housing 20. The clip 136 is affixed to the housing 20 by means of pressure-fitting clip holes 138a, 138b in the front face 46 (shown in FIG. 2) and the back face 77, respectively.

If the treatment site is a surgical wound at the knee joint 132, the end 70 of the desired medicine catheter 62 may be placed directly into the surgical wound by the surgeon at the conclusion of the surgical procedure, but before the wound is closed. Alternatively, the desired medicine catheter 62 may be placed in the treatment site at the knee joint 132 by means of the introducer needle 65 and the insertion catheter 66 while the medicine catheter 62 is free from attachment to any other components of the system 10. In particular, the tip 74 of the introducer needle 65 is inserted through the skin at a surface location proximal to the knee joint 132 with the insertion catheter 66 fitted over the remainder of the introducer needle 65. The tip 74 is pushed under the skin to the treatment site 132 and the introducer needle 65 is then withdrawn from the insertion catheter 66 leaving the tapered end 75 of the insertion catheter 66 in the treatment site 132. The free end 70 of the medicine catheter 62 is inserted into the treatment site 132 through the insertion catheter 66 and the insertion catheter 66 is withdrawn from the treatment site 132 leaving only the end 70 in the treatment site 132. The end 70 of the medicine catheter 62 is fixed in the treatment site 132 by securing an adjacent exposed segment of the medicine catheter 62 to the skin with a strip of tape 140. Setup is completed by finalizing interconnection of the components of the system 10. The compression fitting 67 is attached to the opposite free end 69 of the medicine catheter 62 and the catheter coupling element 68 of the catheter connector 64 is connected to the second extension coupling element 60 of the extension tubing set 16. The extension tube 56 may be threaded underneath the clothing of the patient as shown to minimize interference with patient activity.

In accordance with an alternate embodiment of the present invention, the extension tubing set 16 may be omitted from the medication delivery system 10. The medicine catheter 62 is attached directly to the medicine outlet port 32 by means of the catheter connector 64 or another appropriate coupling. However, the embodiment of the invention, which employs the extension tubing set 16 advantageously enables the medication delivery system 10 to more rapidly deliver a larger volume of a predetermined full dosage of the medicine to the patient than would be possible in the absence of the tubing extension set 16. A relatively long length of the medicine catheter 62 would be required if the medicine catheter 62 were to extend the entire length from the infusion pump 12 to the treatment site. This relatively long length of tubing having a small flow cross-section creates a substantial back pressure which could impede operation of the infusion pump 12 when attempting to deliver large full dosages of the medicine to the treatment site at a relatively rapid rate. By comparison, using the tubing extension set 16 having a large flow cross-section which extends a substantial portion of the distance from the infusion pump 12 to the treatment site enables the delivery of large full dosages of the medicine to the treatment site at a rapid discharge flow rate without substantial impediment. Thus, when using the tubing extension set 16, the medicine catheter 62 desirably has a relatively short length (e.g. about 24 to 18 inches or less), with the tubing extension set 16 making up the remainder of the distance from the infusion pump 12 to the treatment site. The extension tube 56 typically has a length equal to or substantially greater than the length of the medicine catheter 62.

Referring to FIGS. 5A–F, the infusion pump 12 is shown diagrammatically in a sequence of operating modes comprising a single operating cycle, wherein directional arrows are provided to illustrate the flow of the medicine within the infusion pump 12 as appropriate. FIG. 5A shows the infusion pump 12 in the initial inactive mode of operation following setup. The actuator button 40 and displacement piston 96 are in their fully extended upward position while the first and second valves 90, 92 are closed for the duration of the inactive mode. The displacement piston 96 is in its fully extended upward position and the dosage chamber 84 is at its maximum volume filled with a full dosage of the medicine for the duration of the inactive mode of operation. When the dosage chamber 84 is filled as in FIG. 5A, the upper liquid level 142 of the medicine contacts the bottom 108 of the displacement piston 96. The displacement piston 96 is blocked from further upward movement by engagement of the first stop 104a of the actuator button 40 with the first stop 104b of the housing 20, irrespective of whether the biasing spring 98 continues to apply the upward displacement force to the displacement piston 96. There is essentially no flow of the medicine through the fluid flowpath of the infusion pump 12 for the duration of the inactive mode of operation and the entire fluid flowpath, including the fluid reservoir 82 and dosage chamber 84, remains at ambient atmospheric pressure.

FIG. 5B shows the infusion pump 12 at the precise time when the system 10 has transitioned from the inactive mode of operation to the dosage discharge mode of operation. The patient initiates the dosage discharge mode of operation by steadily and firmly applying a downward force with the hand to the actuator button 40, which is sufficient to overcome the resistance of the actuator button 40. A number of forces contribute to the resistance of the actuator button 40 including the displacement force of the biasing spring 98 and the resistance of the displacement piston 96. Manual depression of the actuator button 40 impinges on the top of the displacement piston 96, downwardly displacing the displacement piston 96 away from its fully extended upward position. Downward displacement of the displacement piston 96 correspondingly reduces the volume of the dosage chamber 84, driving the medicine from the dosage chamber 84 through the second valve 92, which is open for the duration of the dosage discharge mode of operation while the first valve 90 remains closed. The medicine continues out the medicine outlet port 32 through the extension tube 56 and the medicine catheter 62 until the medicine ultimately reaches the treatment site. The medicine is not permitted to flow from the dosage chamber 84 back into the fluid reservoir 82 in any substantial quantity during the dosage discharge mode of operation due to a back pressure created by the flow restrictor 94.

FIG. 5C shows the infusion pump 12 when the system 10 is completing the dosage discharge mode of operation immediately before transitioning to the dosage charge mode of operation. The first valve 90 remains closed while the second valve 92 remains open. The actuator button 40 is manually depressed until the actuator button 40 and displacement piston 96 are downwardly displaced to their fully depressed downward position. As a result, the dosage chamber 84 is reduced to its minimum volume and the full dosage of the medicine is delivered from the dosage chamber 84 to the treatment site.

As shown in FIG. 5D, the system 10 automatically and immediately transitions to the dosage charge mode of operation when the actuator button 40 is manually released by the patient at the completion of the dosage discharge mode of operation. The second valve 92 closes while the first valve 90 remains closed at the outset of the dosage charge mode of operation. The biasing spring 98 also rapidly expands to the less stressed position, which immediately returns the actuator button 40 and displacement piston 96 to their fully extended upward position and returns the dosage chamber 84 to its maximum volume at the outset of the dosage charge mode of operation. Because the first and second valves 90, 92 are closed, full extension of the displacement piston 96 to its upward position creates a void constituting a near total vacuum of extremely reduced pressure relative to the fluid reservoir 82, which remains at ambient atmospheric pressure. The positive pressure differential between the fluid reservoir 82 and the dosage chamber 84 creates a suction force in the dosage chamber 84, which acts on the medicine in the fluid reservoir 82 to begin drawing the medicine into the dosage chamber 84 through the charge flowpath at a steady maximum charge flow rate.

FIG. 5E shows the infusion pump 12 at the approximate midpoint in time of the dosage charge mode of operation. The first and second valves 90, 92 remain closed, while the biasing spring 98 remains less stressed and the actuator button 40 and displacement piston 96 remain in their fully extended upward position. The liquid level 142 of the medicine in the dosage chamber 84 is at the volumetric midpoint of the dosage chamber 84 with the remainder of the dosage chamber volume occupied by the void. Because the void constitutes a near total vacuum, the positive pressure differential is maintained between the fluid reservoir 82 and the dosage chamber 84 which correspondingly maintains the suction force constant in the dosage chamber 84. The constant suction force in conjunction with the flow restrictor 74 produces a continuous and constant maximum charge flow rate at which the medicine is drawn into the dosage chamber 84 throughout the dosage charge mode of operation. As such, the suction force has drawn about half the predetermined volume of a full dosage of the medicine from the fluid reservoir 82 into the dosage chamber 84 at the approximate midpoint in time of the dosage charge mode of operation.

FIG. 5F shows the infusion pump 12 when the system 10 is completing the dosage charge mode of operation immediately before transitioning to the inactive mode of operation. When the maximum charge flow rate and maximum volume of the dosage chamber 84 is as recited above, the total elapsed time of the dosage charge mode, termed the full dosage charge time, is about 30 minutes. This is the time required for the dosage chamber 84 to receive a full dosage of the medicine from the fluid reservoir 82 via the flow restrictor 94 after initiating the dosage charge mode of operation. Filling the dosage chamber 82 with a full dosage of the medicine eliminates the void and substantially equalizes the pressure between the fluid reservoir 82 and the dosage chamber 84 at ambient atmospheric pressure, thereby terminating the dosage charge mode of operation and returning the system 10 to the inactive mode of operation. In sum, FIGS. 5A–F demonstrate one complete operating cycle of the system 10.

The operating cycles of the system 10 may be repeated as often as needed until the total medicine charge in the fluid reservoir 82 is exhausted as observed through the windows 44 or until additional medicine is no longer required at the treatment site. The total medicine charge will typically provide a treatment period of several hours to a few days depending on the needs of the patient. If the patient requires further treatment after exhaustion of the total medicine charge, the health care provider may recharge the system 10 with medicine in substantially the same manner as described above with respect to system setup. However, the system 10 is only intended for single patient use. When the treatment is terminated for a given patient, the system 10 is removed from the patient and preferably disposed. The system 10 is constructed from relatively low-cost, disposable materials which may be cost-effectively discarded or destroyed after single patient use, thereby avoiding the risk of infection or other complications caused by multiple patient use.

As described above, FIGS. 5B and 5C show the patient self-administering a full dosage of the medicine from the dosage chamber 84 after the system 10 has transitioned to the inactive mode of operation. It is further within the scope of the present invention for the patient to self-administer a partial dosage, i.e., less than a full or bolus dosage, of the medicine from the dosage chamber 84 after the system 10 has transitioned to the inactive mode. To self-administer a partial dosage of the medicine, the patient only partially depresses the actuator button 40 to a desired partially depressed downward position which corresponds to the desired partial dosage. The scale 42 may be used as a guide to determine when the desired partially depressed downward level and the desired partial dosage have been achieved. Thereafter, the actuator button 40 is released and the infusion pump 12 retransitions to the dosage charge mode of operation in the manner described above.

Although it is generally preferred that the patient self-administer the medicine from the dosage chamber 84 in accordance with FIGS. 5B and 5C after the system 10 has transitioned to the inactive mode of operation, it is within the scope of the present invention for the patient to self-administer the medicine from the dosage chamber 84 while the system 10 is still in the dosage charge mode of operation.

An advantageous feature of the present invention is the overmedication prevention mechanism provided by the flow restrictor 94. Although the patient is free to self-administer the medicine at any time after the dosage charge mode is initiated, the patient can only self-administer as much medicine at a given time as is present in the dosage chamber 84. The flow restrictor 94 limits the maximum charge flow rate of the medicine into the dosage chamber 84 from the fluid reservoir 82 to a level, which preferably corresponds to the desired dosage rate of the medicine to the patient. Consequently, the patient is unable to self-administer the medicine at a rate, which exceeds the maximum desired dosage rate, no matter how often the patient fully depresses the actuator button 40 during operation of the system 10. For example, if the maximum desired dosage rate of the medicine is a bolus dosage of 16 cc every 2 hours (8 cc per hour on average) and a dosage chamber 82 is provided having a maximum volume of 4 cc, a flow restrictor 94 is preferably selected having a charge flow rate of 8 cc per hour. If the patient fully depresses the actuator button 40 every 7.5 minutes for 2 hours, the patient only receives a partial dosage of 1 cc at each interval, which corresponds to an average dosage rate of 8 cc per hour. Alternatively, if the patient fully depresses the actuator button 40 every 3.75 minutes for 2 hours, the patient only receives a partial dosage of 0.5 cc at each interval, which still corresponds to an average dosage rate of 8 cc per hour.

The present invention has been described above in terms of specific preferred embodiments of medication delivery systems having infusion pumps. In broad terms, however, the invention is deemed to generally include substantially all medication delivery systems employing infusion pumps having a fluid reservoir, a dosage chamber and a charge flowpath therebetween, which includes a flow restrictor selectively configured by the practitioner with respect to length and cross-section to regulate the charge flow rate of a liquid medicine through the charge flowpath from the fluid reservoir to the dosage chamber in correspondence with the desired dosage rate of the liquid medicine to the treatment site. The liquid medicine is driven through the charge flowpath by means of a positive pressure differential between the fluid reservoir and dosage chamber, which is created by depressurizing the dosage chamber.

While the forgoing preferred embodiments of the invention have been described and shown, it is understood that alternatives and modifications, such as those suggested and others, may be made thereto and fall within the scope of the invention.

We claim:

1. An infusion pump for delivering a medical treatment fluid to a patient comprising:

a flexible fluid reservoir for storing a medical treatment fluid, said fluid reservoir having a medical treatment fluid inlet port and an inlet valve with an open position and a closed position;

a rigid dosage chamber having a fluid outlet for the medical treatment fluid;

a displacement piston displacable within said dosage chamber, a charge flowpath providing fluid communication between said fluid reservoir and said dosage chamber, said charge flowpath including a flow restrictor; and an elastic member connected to said displacement piston, said elastic member transitionable from a more stressed position to a less stressed position to charge said dosage chamber with the medical treatment fluid from said fluid reservoir at a charge flow rate controlled by said flow restrictor while said inlet valve remains in said closed position blocking said medical treatment fluid inlet port and transitionable from said less stressed position to said more stressed position to discharge the medical treatment fluid from said dosage chamber via said fluid outlet, wherein said elastic member displaces said displacement piston in a first direction away from said fluid outlet to expand said dosage chamber when said elastic member transitions from said more stressed position to said less stressed position, and wherein said displacement piston is displaced in a second direction toward said fluid outlet to contract said dosage chamber when said elastic member transitions from said less stressed position to said more stressed position.

2. The infusion pump of claim 1 wherein said flow restrictor is a passive device having a fixed length and a fixed cross-section, wherein said fixed length and said fixed cross-section are selected to produce the controlled charge flow rate of the medical treatment fluid through said charge flowpath into said dosage chamber.

3. The infusion pump of claim 1 wherein said flow restrictor is a continuously open length of flexible tubing.

4. The infusion pump of claim 1 wherein said fluid reservoir is a substantially inelastic bladder.

5. The infusion pump of claim 1 wherein said elastic member is a spring.

6. A medication delivery system comprising:
an infusion pump including,
  a flexible fluid reservoir for storing a treatment fluid, said fluid reservoir having a treatment fluid inlet port and an inlet valve with an open position and a closed position,
  a rigid dosage chamber having a fluid outlet for the treatment fluid,
  a displacement piston slidably displacable within said dosage chamber,
  a charge flowpath providing fluid communication between said fluid reservoir and said dosage chamber, said charge flowpath including a flow restrictor; and
  an elastic member connected to said displacement piston, said elastic member transitionable from a more stressed position to a less stressed position to charge said dosage chamber with said treatment fluid from said fluid reservoir at a charge flow rate controlled by said flow restrictor while said inlet valve remains in said closed position blocking said treatment fluid inlet port and transitionable from said less stressed position to said more stressed position to discharge said treatment fluid from said dosage chamber via said fluid outlet, wherein said elastic member displaces said displacement piston in a first direction away from said fluid outlet to expand said dosage chamber when said elastic member transitions from said more stressed position to said less stressed position, and wherein said displacement piston is displaced in a second direction toward said fluid outlet to contract said dosage chamber when said elastic member transitions from said less stressed position to said more stressed position; and
a medicine catheter having first and second ends, wherein said medicine catheter is in fluid communication with said fluid outlet of said dosage chamber, and wherein said first end of said medicine catheter is positionable in a treatment site of a patient to deliver the treatment fluid to the treatment site.

7. The medication delivery system of claim 6 wherein said flow restrictor is a passive device having a fixed length and a fixed cross-section, wherein said fixed length and said fixed cross-section are selected to produce the controlled charge flow rate of the medical treatment fluid through said charge flowpath into said dosage chamber.

8. The medication delivery system of claim 6 wherein said flow restrictor is a continuously open length of flexible tubing.

9. The medication delivery system of claim 6 wherein said fluid reservoir is a substantially inelastic bladder.

10. An infusion pump for delivering a medical treatment fluid to a patient comprising:
  a fluid reservoir;
  a dosage chamber;
  a displacement piston displacable within said dosage chamber;
  a charge flowpath providing fluid communication between said fluid reservoir and said dosage chamber, said charge flowpath including a passive flow restrictor; and
  an elastic member connected to said displacement piston, said elastic member transitionable from a more stressed position to a less stressed position to charge said dosage chamber with the medical treatment fluid from said fluid reservoir at a charge flow rate controlled by said passive flow restrictor and transitionable from said less stressed position to said more stressed position to discharge the medical treatment fluid from said dosage chamber, wherein said elastic member displaces said displacement piston in a first direction to expand said dosage chamber when said elastic member transitions from said more stressed position to said less stressed position, and wherein said displacement piston is displaced in a second direction to contract said dosage chamber when said elastic member transitions from said less stressed position to said more stressed position.

11. The infusion pump of claim 10 wherein said passive flow restrictor has a fixed length and a fixed cross-section, wherein said fixed length and said fixed cross-section are selected to produce the controlled charge flow rate of the medical treatment fluid through said charge flowpath into said dosage chamber.

12. The infusion pump of claim 10 wherein said passive flow restrictor is a continuously open length of flexible tubing.

13. The infusion pump of claim 10 wherein said fluid reservoir is a substantially inelastic bladder.

14. The infusion pump of claim 10 wherein said elastic member is a spring.

15. An infusion pump for delivering a medical treatment fluid to a patient comprising:
  a fluid reservoir;
  a dosage chamber;
  a displacement piston displacable within said dosage chamber;
  a charge flowpath providing fluid communication between said fluid reservoir and said dosage chamber, said charge flowpath including a passive flow restrictor having a fixed length and a fixed cross-section; and
  an elastic member connected to said displacement piston, said elastic member transitionable from a more stressed position to a less stressed position to charge said dosage chamber with the medical treatment fluid from said fluid reservoir at a charge flow rate controlled by said passive flow restrictor, wherein said fixed length and said fixed cross-section are selected to produce the controlled charge flow rate.

16. The infusion pump of claim 15 wherein said passive flow restrictor is a continuously open length of flexible tubing.

17. The infusion pump of claim 15 wherein said fluid reservoir is a substantially inelastic bladder.

18. A method for charging a dosage chamber of an infusion pump with a liquid medical treatment fluid comprising:

providing a fluid reservoir containing a liquid medical treatment fluid and a dosage chamber containing a displacement piston;

providing fluid communication between said fluid reservoir and said dosage chamber via a charge flowpath, said charge flowpath including a passive flow restrictor having a fixed length and a fixed cross-section;

displacing said displacement piston in said displacement chamber to create a positive pressure differential between said fluid reservoir and said dosage chamber; and driving said medical treatment fluid from said fluid reservoir through said charge flowpath into said dosage chamber by said positive pressure differential at a charge flow rate controlled by said passive flow restrictor, wherein said fixed length and said fixed cross-section are selected to produce said controlled charge flow rate.

19. The method of claim 18 wherein said controlled charge flow rate corresponds to a desired dosage rate of said medical treatment fluid to a patient.

20. The method of claim 18 wherein said controlled charge flow rate is substantially constant.

21. The method of claim 18 wherein said displacement piston is displaced by transitioning an elastic member connected to said displacement piston from a more stressed position to a less stressed position.

22. The method of claim 18 wherein displacement of said displacement piston creates a void in said dosage member of extremely reduced pressure relative to said fluid reservoir.

23. The method of claim 18 wherein displacement of said displacement piston creates a void constituting a near total vacuum.

24. The method of claim 18 wherein said fluid reservoir is maintained at substantially ambient atmospheric pressure.

* * * * *